US006801316B2

United States Patent
Guthermann

(12) United States Patent
(10) Patent No.: US 6,801,316 B2
(45) Date of Patent: Oct. 5, 2004

(54) MEASUREMENT OF AN ANALYTE CONCENTRATION IN A SCATTERING MEDIUM

(75) Inventor: Howard E. Guthermann, Newton, MA (US)

(73) Assignee: Optix LP, Jupiter, FL (US)

( * ) Notice: Subject to any disclaimer, the term of this patent is extended or adjusted under 35 U.S.C. 154(b) by 0 days.

(21) Appl. No.: 10/198,889

(22) Filed: Jul. 19, 2002

(65) Prior Publication Data

US 2004/0012789 A1 Jan. 22, 2004

(51) Int. Cl.[7] .............................................. G01N 21/49

(52) U.S. Cl. ..................................................... 356/437

(58) Field of Search .......................... 356/39, 405, 437; 250/343; 600/310, 316, 322

(56) References Cited

U.S. PATENT DOCUMENTS 5,818,048 A * 10/1998 Sodickson et al. .......... 250/343
6,087,182 A * 7/2000 Jeng et al. .................... 436/66

* cited by examiner

Primary Examiner—Richard A. Rosenberger
(74) Attorney, Agent, or Firm—Palmer & Dodge LLP; Ralph A. Loren, Esq.

(57) ABSTRACT

A non-invasive detection method for glucose and other constituents of interest in a sample is described. The apparatus and methods of the invention provide an analog of color perception of human vision, preferably in the near infrared region, replacing the spectrophotometers used in other non-invasive near infrared detection methods. A plurality of detection units are used, each covering a broad region of the detected spectrum, paralleling color perception and colorimetry. In some circumstances, a neural net is used for analysis, allowing the system to learn. Analyte concentrations in scattering mediums can be obtained by calibrating the results with in vitro measurements.

38 Claims, 8 Drawing Sheets

MEASUREMENT OF AN ANALYTE CONCENTRATION IN A SCATTERING MEDIUM

BACKGROUND OF THE INVENTION

Testing of a human sample, such as a blood sample, to determine a concentration of a particular analyte in the sample is widespread. Most of these tests are invasive in that they require the removal of, or intrusion into some tissue. For example, a conventional blood test involves the perforation of the skin with a hypodermic needle to withdraw blood. The blood sample is then examined in the laboratory to determine the concentration of some analyte, such as glucose, in the blood.

Such invasive procedures have several drawbacks associated with inconvenience, cost, and pain. Patients often detest or outright avoid the procedures. For example, many diabetics must test their blood glucose levels four or more times a day. The modern battery powered instruments for home use require a finger prick to obtain the sample. The extracted blood sample is then placed on a chemically treated carrier that is inserted into the instrument to obtain a glucose reading. This finger prick is painful and can be a problem when required often. In addition, although the price has dropped considerably on these instruments, the cost for the disposables and the mess and health risks associated with having open bleeding is undesirable. As a result, patients are reluctant to undergo such tests.

The spread of acquired immunodeficiency disease syndrome (AIDS), and the associated fear among public and healthcare personnel of AIDS has made many people afraid of invasive procedures. Not only can diseases such as AIDS be spread with invasive procedures if proper precautions are not followed, hepatitis and other similar blood diseases are more common problems in this type of testing. Nurses, for example, have been known to unintentionally transmit hepatitis from one patient to another with a sampling device itself. This type of disease transfer is eliminated with non-invasive testing.

Development of non-invasive testing methods has become an important topic in the last several years. Accordingly, a number of groups have recently tried to make non-invasive instruments for testing a variety of analytes. A recent trend in non-invasive testing has been to explore the use of the near infrared spectral region (700–2500 nm), more particularly the range from 700–1700 nm. For example, testing involving classical spectrophotometric techniques, such as disclosed in U.S. Pat. No. 5,054,487, by Clarke, and U.S. Pat. No. 5,028,787, by Rosenthal et al., have been employed. These spectrophotometric methods utilize a set of narrow wavelength sources, or scanning spectrophotometers, which scan wavelength by wavelength across a broad spectrum. The data obtained from these methods are spectra, which then require substantial data processing to eliminate background.

One problem with using these types of methods is that spectrophotometers were conceived primarily for accurate determination, in terms of wavelength, of the spectral structure, rather than for discriminating the presence of weak broadband features in strong broadband backgrounds. Since in non-invasive testing for glucose and other materials the primary information sought is the concentration, those using spectrophotometric methods here had to resort to using a number of unsatisfactory analysis techniques to suppress unwanted interference and to calculate the amplitude of the signal.

To overcome such shortcomings of conventional spectrophotometric techniques, other non-invasive methods that are analogous to colorimetry were provided in U.S. Pat. No. 5,321,265, by Block, and U.S. Pat. No. 5,424,545, by Block and Sodickson, incorporated herein by reference. These last methods, dubbed Kromoscopy™, obtain the raw data in the infrared in a manner more similar to the way the eye discriminates color in the visible, than classic spectrophotometric measurements. Colorimetry uses three dimensions to describe the color. There presently are several such three dimensional spaces in use. One of these three dimensional spaces is the CIE 1931 (x,y)-chromaticity diagram, which is based on the light sensitivities of the cones in the eye. It is the trivariant nature of color vision that permits color to be specified in a three dimensional space. Another three-dimensional space involves hue, chroma and value. An analog of colorimetry, particularly one in the infrared region that involves measuring absorbance/transmission of infrared light through a human sample containing blood, shows similar usefulness in determining analyte concentration, as described in the last two patents.

Kromoscopy yields an n-dimensional vector, or Kolor vector, of an analyte that is indicative of the concentration of the analyte. The Kolor vector is the analog of the three component CIE vector mentioned above, except that n is determined by the number of detection channels used and can therefore be made larger than three.

These non-invasive testing procedures patterned after colorimetry, while useful, have some drawbacks when in vivo measurements are attempted. Light travelling through skin and tissue is scattered. In addition, the presence of particles in blood that can also scatter the infrared light complicates measurements of analyte concentrations. Since many scatterers exist in blood, this effect can be quite troublesome. Thus, there exists a need for spectral systems and methods that can measure analyte concentration in a medium that gives rise to significant scattering of light. Such systems and methods would be particularly useful because the type of medium likely to be encountered in a clinical setting gives rise to significant scattering of light.

SUMMARY OF THE INVENTION

Systems and methods are described herein that can measure the concentration of an analyte in a scattering medium, which measurement is often performed in vivo. The systems and methods are analogous to human color vision, and to colorimetry. The response of the eye is in terms of red, green and blue sensors, the output of which are processed by the eyes and the brain to provide the perception of color. The infrared detection units of the present invention and their response to either transmitted, transflected, or reflected radiation from the sample are analogous to the color sensors of the eye and the color response of the eye, respectively. At least three detection units can be used in the present invention, each having a spectral detection range centered about a different portion of the selected spectrum but with response bands sufficiently wide that there is some overlap with at least one, and preferably more than one, other of the detection units. Moreover, the measurements by the detection units of the transmitted, transflected, or reflected light can be congruent, which means that the volume sampled by each detection unit is substantially the same. Similar to how a CIE vector in colorimetry is indicative of a particular color, the direction and magnitude of a Kolor vector obtained using the principles of the present invention are indicative of the identity and the concentration of an analyte.

The methods of the present invention allow the measurement of an analyte concentration even if the analyte is measured in a scattering medium. The Kolor vector of an analyte in a scattering medium with a particular concentration is not coincident with the Kolor vector of the analyte in a non-scattering medium with the same concentration. The invention recognizes that the angle between the Kolor vector of an analyte in a scattering medium and the Kolor vector of the analyte in a non-scattering medium is significant, measurable, and indicative of the amount of scattering that occurs in the scattering medium. The Kolor vector pertaining to the scattering medium can be made co-directional with the Kolor vector pertaining to the non-scattering medium by a rotation that can be specified by a correction vector Δ. A useful property of Δ is that it is independent of the particular analyte being measured. Thus, having obtained Δ, the Kolor vector of a trace analyte, such as glucose, obtained in a measurement performed with the same scattering medium, can be transformed to its corresponding in vitro Kolor vector. The same scattering medium, in this context, means that the scattering properties present during the measurement of Δ and during the measurement of the Kolor vector of the trace analyte are substantially the same. The variability of the sample in vivo, both over time and space, may require that the two measurements be close in time. However, in other situations where the scattering properties might be more stable (e.g., pharmaceutical measurements, fermentation systems) this restriction of being close in time could be relaxed. A standard, such as water, can therefore be used to obtain a correction vector that transforms data obtained in the scattering medium to corresponding data in a non-scattering medium.

In this manner, the present invention allows non-invasive, in vivo identification of analytes and measurements of analyte concentration in a scattering medium. Analytes such as glucose, alcohol, drugs of abuse or other materials can be tested in a non-invasive manner. These methods are particularly well adapted for use in the home glucose testing market since they do not require a finger puncture to obtain a separable blood sample but rather can be utilized without bodily invasion.

In particular, a system and method for measuring the concentration of an analyte in a scattering medium are described herein. The system and method involve illuminating a sample containing the analyte with broad spectrum radiation, and detecting an amount of transmitted, transflected, or reflected radiation from the sample with a detector. In one embodiment, at least three detection units, which can include broad bandpass filters, may be used, each detection unit having a peak spectral response in a separate portion of the spectrum. The step of detecting can include impinging the radiation transmitted, transflected, or reflected from the sample onto the detector that includes a plurality of detection units each responsive to a specific region of a spectrum associated with the transmitted, transflected, or reflected radiation. The spectral response of each of the detection units have at least a partial overlap with the response of at least one other of the detection units. The detecting step may also include impinging the radiation transmitted, transflected, or reflected from the sample onto the detector that includes a plurality of filters, each of the filters allowing transmission of a specific region of a spectrum associated with the transmitted or reflected radiation. The spectral response of each of the filters have at least a partial overlap with the response of at least one other of the filters, wherein each of the filters is impinged on the radiation transmitted or reflected from the sample or standard sequentially and the output from the detector is used to measure the concentration. The detecting step may involve the use of a black/white detection unit that is responsive to the entire spectrum for which the detection units have a spectral response.

Instead of using n detection units, one detection unit together with a filter module having n filters can be used. In this latter embodiment, the single detection unit detects light during n time periods, which are short relative to the time constants of changes in the sample matrix, such as the pulse rate for in vivo measurements. During the first time period, the filter module passes light associated with a first spectral response. Also during this first time period, the detection unit detects light associated with the first spectral response. This procedure continues analogously for the other n−1 time periods and spectral responses. In both the first embodiment in which n detection units are used, and the second embodiment, in which a single detection unit together with the filter device having n filters are used, n spectral measurements are taken associated with n spectral responses.

The system and method also involves associating a vector in a vector space with the amount of transmitted, transflected, or reflected radiation, and determining a correction vector from a standard in a non-scattering medium. Specifically, the correction vector can be determined from two vectors associated with spectral properties, such as the amount of light absorption by the sample. The first and second vectors are obtained from samples containing the standard in a non-scattering medium, and a scattering medium, respectively.

The system and method further involve utilizing the correction vector and the vector associated with the amount of transmitted, transflected, or reflected radiation to obtain the concentration of the analyte in the scattering medium. Utilizing the correction vector may involve using an artificial analog of a neural network, wherein the artificial neural network is calibrated and trained to process the signals to achieve an analog of color constancy in vision.

The aforementioned methods and systems can be used to non-invasively determine the concentration of the analyte in a human body, in a sample such as a human finger. The analyte can be related to any constituent of fluids, e.g., glucose, glucose indicating constituents, drugs of abuse and drugs of abuse indicating constituents.

DETAILED DESCRIPTION OF THE INVENTION

Methods analogous to colorimetry have been previously described for using radiation to non-invasively measure the concentration of an analyte, such as glucose, in a medium. The methods are most easily employed when the medium does not scatter the light used to make the measurement. The present invention provides calibration for those media that do scatter light. This is an important contribution because in realistic non-invasive measurements, where light is shone on a body part, such as a finger, to measure an analyte in blood, the light is likely to be scattered by the components of the finger and blood. Despite the presence of such scattering, the methods of the present invention permit a non-invasive measurement of the concentration of the analyte. The measurement can be performed in vivo by shining infrared light on a part of the human body, such as a finger.

Similar to how a CIE vector in colorimetry is indicative of a particular color, a Kolor vector obtained using the principles of the present invention is indicative of the concentration and the identity of an analyte. The Kolor vector of an analyte in a scattering medium with a particular concentration is rotated with respect to the Kolor vector of the analyte in a non-scattering medium with the same concentration. The Kolor vector pertaining to the scattering medium can be made co-directional with the Kolor vector pertaining to the non-scattering medium by a rotation that can be specified by a correction vector $\Delta$. For example, when the Kolor space is three-dimensional, $\Delta$ can correspond to the three Euler angles that specify the rotation required to make the Kolor vector pertaining to the scattering medium align with the Kolor vector pertaining to the non-scattering medium.

A useful property of $\Delta$ is that it is independent of the particular analyte being measured. Thus, having obtained $\Delta$ using a standard, the Kolor vector of a trace analyte, such as glucose, obtained in a subsequent measurement performed with a scattering medium can be transformed to its corresponding in vitro (non-scattering) Kolor vector by a rotation defined by $\Delta$. How to obtain the correction vector $\Delta$, and how to use this information to find the analyte concentration, is described below. By this method, the previously unknown Kolor vector direction of the analyte in the scattering medium may be determined, thereby improving the accuracy of the calibration.

Figure 1:
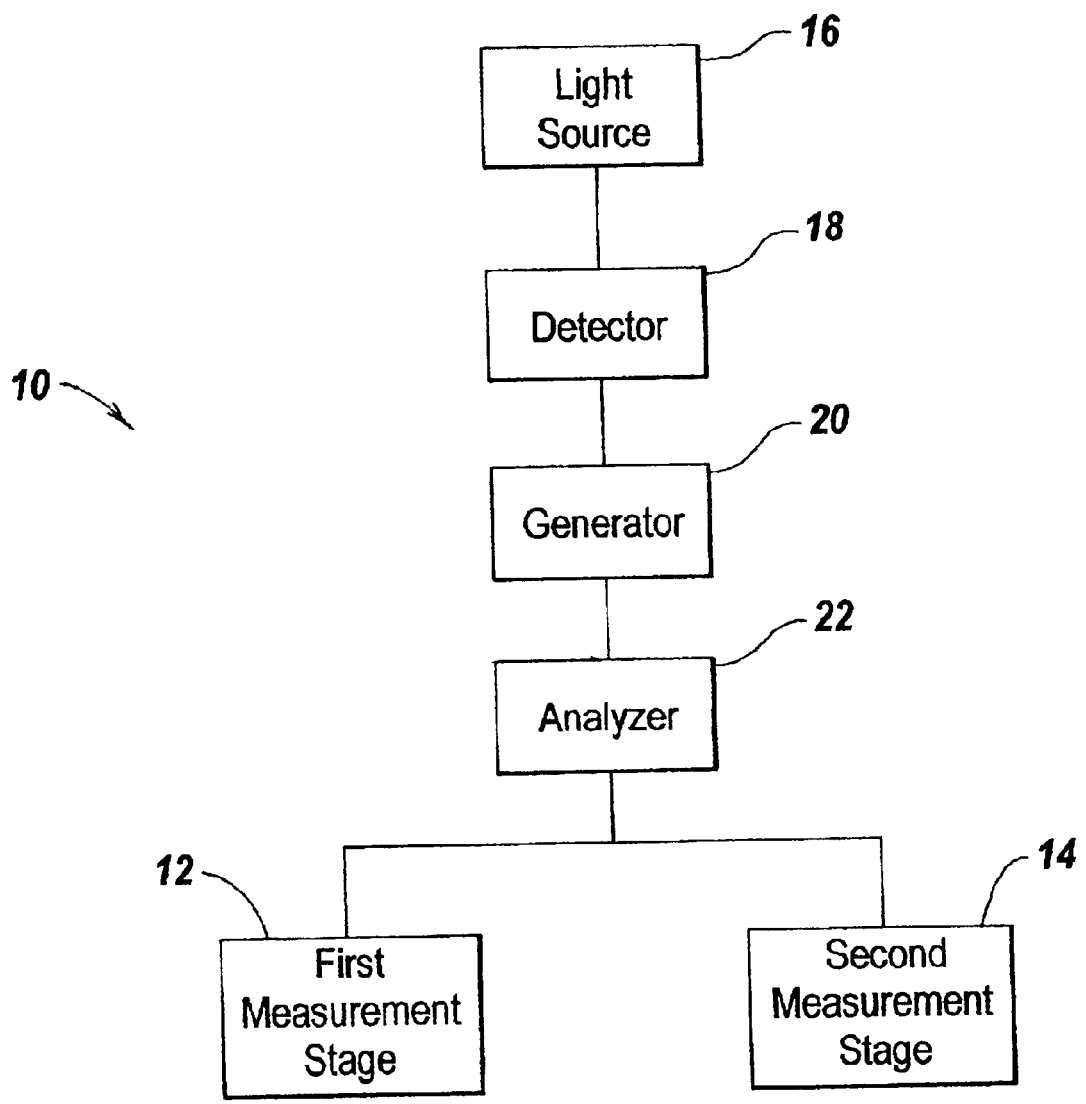
FIG. 1 shows an analyte measuring system for measuring the concentration of an analyte in a scattering medium, according to the teachings of the present invention.

Referring to FIG. 1, an analyte measuring system 10 for measuring the concentration of an analyte in a scattering medium is shown. The system includes a first measurement stage 12, a second measurement stage 14, and a light source 16, such as a tungsten-halogen bulb in a quartz envelope, filtered with a "heat shield," if necessary, to provide only a particular wavelength range. The system 10 further includes a detector 18, a generator 20, and an analyzer 22.

The correction vector is calculated from two vectors, a first vector obtained by the first measurement stage 12 and a second vector obtained by the second measurement stage 14. Specifically, the first measurement stage 12 is used to obtain a first Kolor vector pertaining to a non-scattering medium. The first Kolor vector is associated with a first spectral property of a standard, or calibration substance in a first sample. As detailed in U.S. Pat. Nos. 5,321,265 and 5,424,545, each component of the first Kolor vector corresponds to a measurement by each of the IR detection units or channels. The second measurement stage 14 is used for obtaining a second Kolor vector associated with a second spectral property of the standard in a second sample that does contain the scattering medium. In one embodiment, the standard is water, the scattering medium is blood, and the spectral properties may involve the transmission of light through the samples, or absorption of light by the samples. The first measurement stage 12 can be used for an in vitro measurement, while the second measurement stage 14 can be used for an in vivo measurement.

The light source 16 illuminates a sample containing the analyte with broad spectrum radiation. For example, the sample may include glucose (analyte) dissolved in human blood (medium). In such case, an object of the invention is to measure non-invasively the concentration of glucose in blood in vivo. In another example, the analyte tested can include drugs of abuse, such as alcohol.

The detector 18 is used for detecting transmitted, transflected, or reflected radiation from the sample. The sample may be part of a finger on which light from the light source 16 may be shone. The generator 20 is used for generating a signal corresponding to the detected radiation, and for generating a vector in a vector space (Kolor space) that is associated with the amount of transmitted, transflected, or reflected radiation. The analyzer 22 functions to help obtain the concentration of the analyte in the medium, and can include a computer, hardwired logic circuits, or a neural network. In particular, the analyzer 22 calculates the correction vector A by utilizing the first Kolor vector, and the second Kolor vector, from which, together with the signal, the concentration of the analyte can be calculated as is explained in more detail below. If appropriate, the detector 18 and the generator 20 can be combined into a single device, as can the generator 20 and the analyzer 22.

The analyzer 22 can further use neural networks to more closely approach color perception, as described in U.S. Pat. No. 5,424,545, incorporated herein by reference. While artificial neural networks usually contain hundreds of interconnected neurons, this analog of color perception may only require about two dozen. The learning capacity of the network is advantageous. Since the neural network can "learn," it may be calibrated a single time for the individual, or even have a universal calibration at the factory, and still give consistent results over time. Learning in a neural net context is provided by a change in the way of connections run from one "neuron" to another.

The detector 18 can include a detection array, which generates the signal. The detection array includes a plurality of detection units each responsive to a specific region of a spectrum associated with the transmitted, transflected, or reflected radiation. In a preferred embodiment, the spectral response of each of the detection units has at least partial overlap with the response of at least one other of the detection units, in analogy with the overlapping spectral responses of cones associated with human vision. Moreover, the measurements by the detection units of the transmitted, transflected, or reflected light are preferred to be congruent, which means that each detection unit samples the identical volume of the sample through the same solid angles.

In one embodiment, at least three detection units are used, each detection unit including broad bandpass filters and each having a peak spectral response in a separate portion of the spectrum. Among the detection units can be included a black/white detection unit which is responsive to the entire spectrum for which the detection units have a spectral response.

In this embodiment, the radiation leaving the sample goes to a beam splitter then either directly to a detector array or through a filter before reaching the detector array. The detection array can have four detection units, three of which are filtered in such a way that they have different peak spectral response but some partial overlap of spectral response while the fourth detector constituents a black/white detector. This black/white detector is responsive to all wavelengths in the infrared measurement region for which the other three detectors are responsive; that is, it generates in output signal responsive to wavelengths which cause a response for any of the three other detectors. As such, it acts like the rods of the retina of the eye.

Instead of using n detection units, one detection unit together with a filter module having n filters can be used. In this latter embodiment, the single detection unit detects light during n time periods. During the first time period, the filter module passes light associated with a first spectral response. Also during this first time period, the detection unit detects light associated with the first spectral response. This procedure continues analogously for the other n−1 time periods and spectral responses. In both the first embodiment in which n detection units are used, and the second embodiment, in which a single detection unit together with the filter device having n filters are used, n spectral measurements are taken associated with n spectral responses.

In general, the Kolor change in a sample can be defined as $$R = \sum_j [g(T_j) - g(T_{j0})]f_j, \quad j = 1, \ldots, N$$

where R is the N-dimensional vector representing the Kolor (i.e., the N-dimensional response pattern), T is the optical signal (usually transmission) detected by the jth detection channel, and $f_j$ are the appropriately scaled unit vectors representing unit responses in each of the N detection channels. The subscript 0 represents the components of the initial or reference Kolor of the sample.

The coordinates of a point in Kolor space are functions of the measurement channel responses. The Kolor spaces may have any number of dimensions. The exact form of the function, g, of the channel responses used as the metric to generate the Kolor space for a given analysis is a matter of choice dependent on the analytical goals. The metric is such that the Kolor direction specifies the identity of the analyte, while the Kolor magnitude is related to its concentration. If desired, the functions g can be non-linear combinations of the different channel responses, as appears to occur in mammalian color vision. However, in a preferred embodiment, linear metrics are emphasized, as these simplify the identification and understanding of Kolors.

One example of an analyte that can be subjected to the methods and systems of the present invention is water, which can be the predominant species that absorbs infrared radiation in many solutions. In choosing to investigate radiation absorption by water, it is expected that the primary influence producing changes in Kolor direction would be the relative effects of scattering in the different detection channels, and that these effects would, to a first approximation, be dependent only on the total absorption, and not on the individual absorptions by each analyte. The larger absorbance changes simplify the measurement problem, compared with that for a trace analyte such as glucose. The primary simplification is that, since water is the predominant absorbing species, it can be inferred that variations in the Kolor of the in vivo samples result predominantly from changes in water pathlength and concentration.

Figure 3:
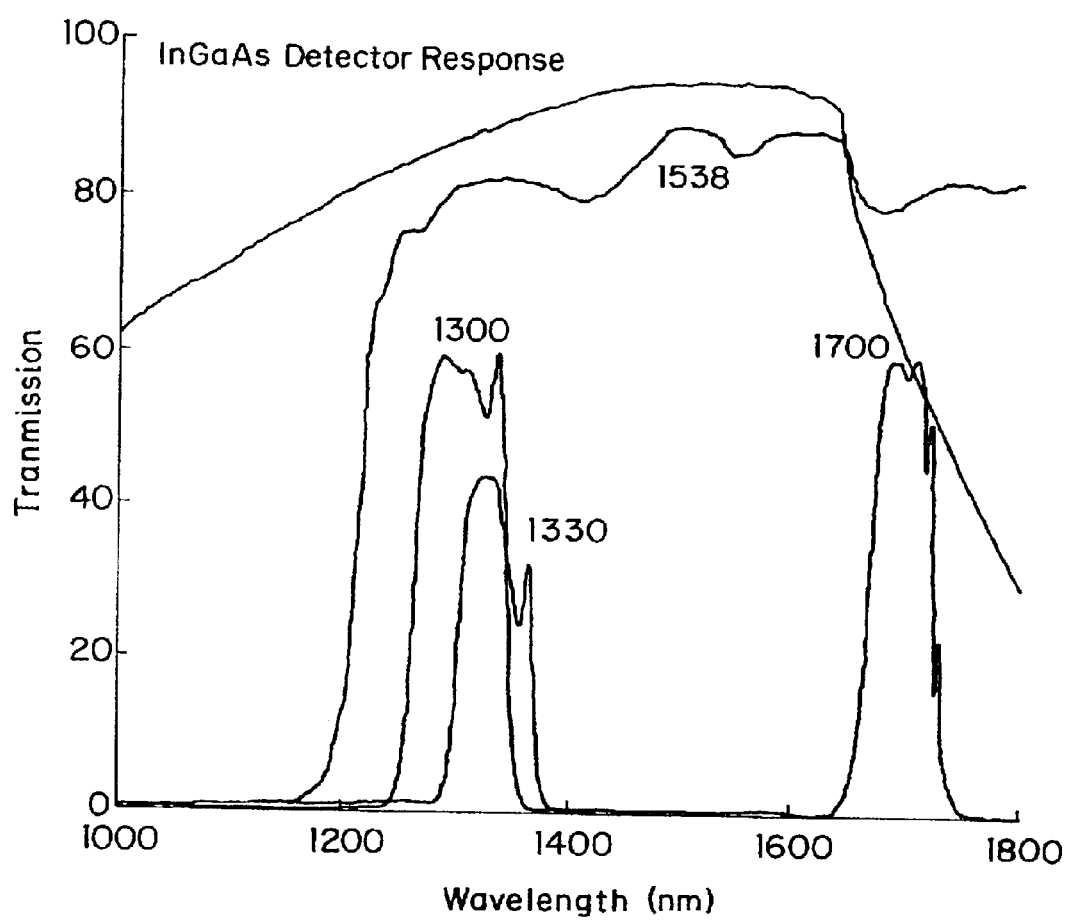
FIG. 3 shows the spectral responses of a set of filters used to obtain the analyte concentration, according to the teachings of the present invention.

The filters defining the Kolor space can be chosen based on a preliminary investigation of over fifty different broadband (filter width at half-maximum transmittance>50 nm) filters. The responses of detection channels with these filters to changes in glucose and in water concentration (simulated by addition of deuterium oxide to water) are combined and permuted in a computer simulation. The best combination of four filters, as measured by response to changes in glucose concentration in a direction orthogonal to the Kolor of water, the major interferent, is shown in FIG. 3, along with the spectral sensitivity of the detectors use. In FIG. 3, the filters centered on 1300, 1330, and 1700 nm were obtained from Omega Optical, Brattleboro, Vt., and had bandwidths (full-width at half maximum response) of 100 nm, 70 nm, and 50 nm, respectively. The broad filter labeled 1538 was obtained from Optical Filter Corporation of Natick, Mass.

Measurement of the Kolor direction of pure water in vitro using several metrics, and in vivo using parallel metrics are now described. The in vivo measurements have a pulsatile or systolic component and a steady or diastolic component. The systolic component provides a measurement on changes in blood volume in the optical path. The diastolic component provides a measurement of all constituents in the probing light path. The comparative Kolor directions in the different metrics for each of these components are also described.

First Measurement Stage for In Vitro Kolor Measurement

Figure 2:
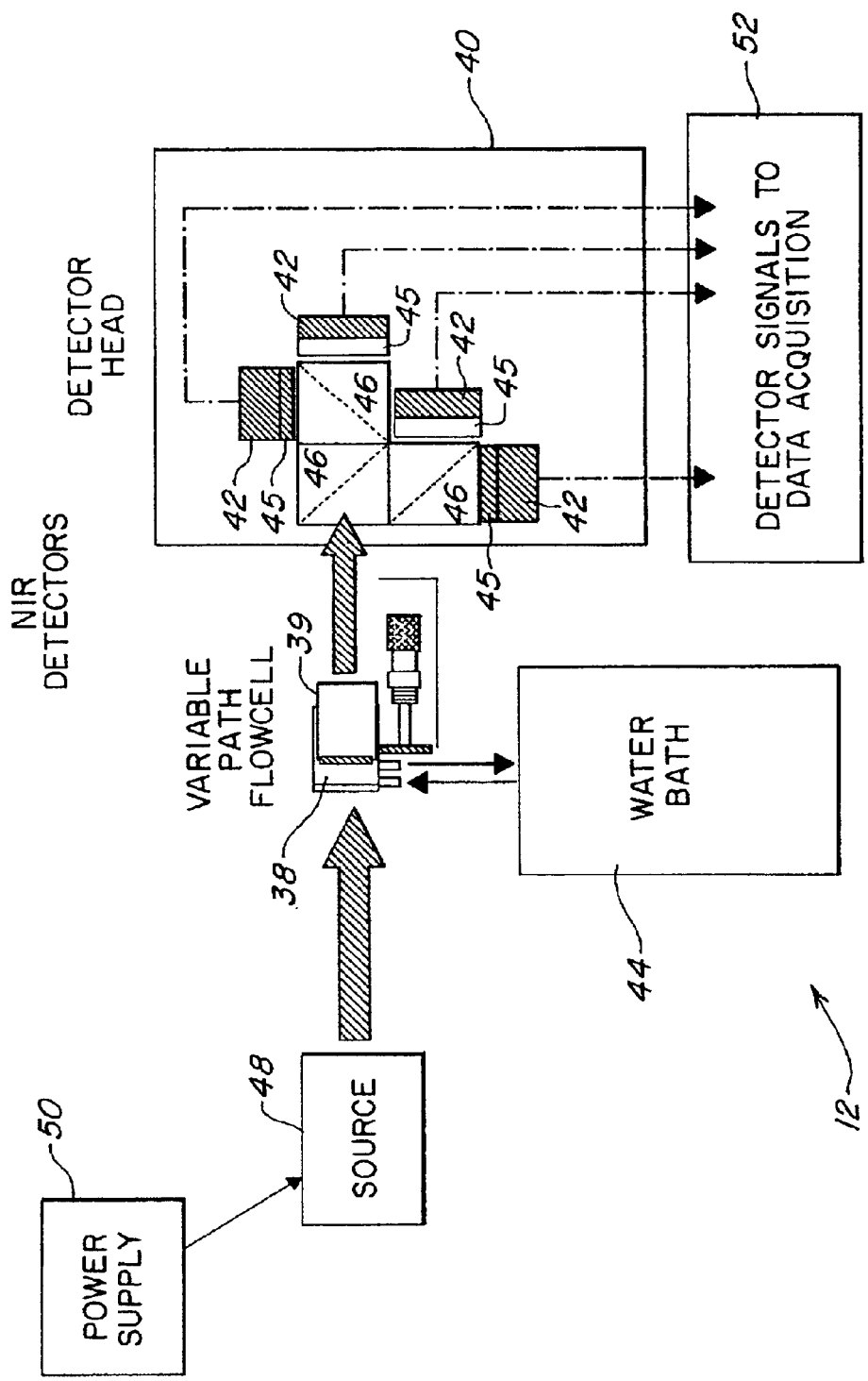
FIG. 2 shows a first measurement stage that appears in FIG. 1 for obtaining a spectral property of a standard.

Referring to FIG. 2, the first measurement stage 12, used to obtain a first Kolor vector associated with a first spectral property of water in a first sample 38 is shown. The first measurement stage 12 is used to obtain a Kolor vector associated with a concentration of an analyte, such as water, in a non-scattering medium.

The first measurement stage 12 includes a four-channel assembly 40 using 5 mm diameter InGaAs photodiodes 42 (Hamamatsu G5832-05, Bridgewater, N.J.) maintained at room temperature by a water bath 44. The water bath 44 is used for fluid handling and temperature control, and can include a constant temperature circulating water bath (Model 12105, Cole-Parmer, Vernon Hills, Ill.) supplying a variable pathlength flow cell 39, which includes the first sample 38, with 38° C. water at approximately 3 liters per minute. In front of each detector 42 is a broadband optical filter 45.

The first measurement stage 12 further includes a beam splitter assembly 46. This assembly 46 is designed so that each detector 42 is illuminated with the radiation passing through the first sample that has the same spatial and angular distribution. The beam splitter assembly 46 is fabricated for optimal spectral flatness in the near-infrared portion of the spectrum. The optical source 48 includes a 20-watt flat filament lamp (Gilway 7416, Woburn, Mass.) powered by a constant current power supply 50 (Oriel 68831, Stamford, Conn.). Lenses collimate the light passing through the flow cell and focus that light onto the detectors 42 through the beamsplitter assembly 46.

The first measurement stage 12 also includes a data acquisition system 52 comprising four high-resolution voltmeters (Hewlett-Packard 3458A, Sunnyvale, Calif.) connected via a GPIB bus to a Pentium PC. The HP voltmeters are capable of over 22 bits of resolution at 50 Hz, and are programmed for optimal simultaneity in sampling.

The variable pathlength flow cell (VPFC) 39 includes a fixed sapphire window on one side and a sliding cylinder with an attached sapphire window on the other side. An attached micrometer controls the distance between the sapphire windows, the in vitro pathlength.

FIG. 3 shows the spectral responses of the set of filters 45 used for both the in vitro (non-scattering medium) and in vivo (scattering medium) experiments. The filter designations indicate the approximate center wavelength of the broad transmission bands.

The first measurement stage 12 takes in vitro data at initial micrometer settings of 1.5, 5.5, 10, 11, 14, 17, and 20 mm. At each pathlength setting, two-minute data sets are taken between changes in pathlength of either 0.25 mm or 0.10 mm for a total pathlength change of 1.0 mm with respect to the initial setting. A digital low pass filter is applied to each individual channel of the data runs before averaging.

One metric for water Kolor can be obtained by measuring the relative response in each channel. For example, a Kolor can be created by the difference in transmission between data sets representing a pathlength change of one millimeter divided by the signal level at the shortest pathlength.

Vectors associated with the three-dimensional Kolor space defined by this metric for the 1300, 1330, and 1538 filter channels can be calculated. The largest angle between these Kolor vectors is approximately 4°. The mean angular difference is approximately 1°.

Another metric for water Kolor can be obtained from the in vitro data by measuring the absolute difference between transmission levels for a given pathlength change. Since this is an absolute measure it is a non-linear function of pathlength and dependent on both the total pathlength and the differential pathlength used. Despite these issues, the in vivo analog to this measure is independent of the background measurements, and it may therefore be of utility in interpreting the in vivo data.

Second Measurement Stage for In Vivo Kolor Measurement

The instrumentation of the second measurement stage 14 and the data acquisition protocol for the in vivo measurements is parallel to that described above for the in vitro measurements. The differences, which result from differences in properties between the aqueous in vitro samples and the in vivo sampling sites (the distal joint of the fingers of the left hand), are described below.

The photodetectors 42 in the first measurement stage 12 can also be used in the second measurement stage 14; however, the detection channels can be provided with different gains to compensate for the lower transmission levels measured in this spectral region in vivo. The effects of these gain changes are compensated for in the computation of the measured Kolor directions.

The higher frequency of variation inherent in the in vivo optical signals also suggests a change in the sampling frequency. Rather than the 50 Hz sampling performed in vitro, the in vivo data is taken at 1000 Hz over thirty seconds to assure proper delineation of the pulsatile signals. Careful construction of the measurement triggering system assures that temporal congruency of sampling is achieved to within 5 microseconds, less than 1% of the sample frequency.

The major differences between the first measurement stage 12 and the second measurement stage 14 involve the sample holder included in the first measurement stage 12 for the first sample and the sample holder included in the second measurement stage 14 for the second sample. A custom designed finger holder replaced the variable pathlength flow cell 39 shown in FIG. 2. In the finger holder, four segments of 12.7 mm ID thin-walled silicone tubing were connected in series and were maintained by a plastic housing parallel to the longitudinal axis of the finger, and at the four corners of a rectangle circumscribing the finger from an end-on view. The four tubing segments are attached in series to a controlled pressure air source. Inflation of the tubing to approximately 15 kPa, combined with the frictional forces between the finger and the tubing, restrained fingers of a variety of thicknesses.

A variety of light sources can be employed with this configuration. The best results, as measured by increases in the relative eigenvalues of the first to the sum of the remaining principal components of the data, were obtained using two micro-axial lead lamps (Gilway 7515, 1 mm diameter by 5 mm length, rated output 80 mW, color temperature 2000 K) connected in parallel and taped in parallel, with opaque photographic tape, across the base of the fingernail.

Kolor Metrics

Figure 4:
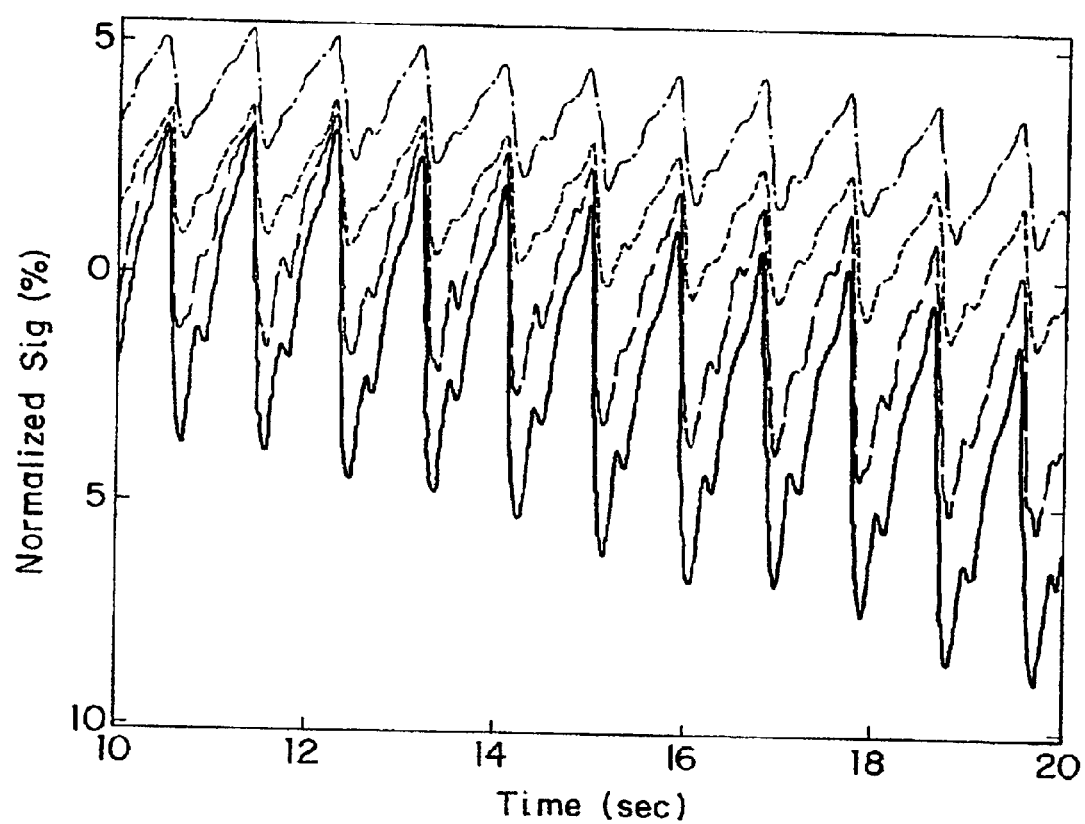
FIG. 4 shows data from an in vivo experiment displaying the pulsatile response to cardiac pressure changes.

The raw data from a typical in vivo experiment is shown in FIG. 4, displaying the pulsatile response to cardiac pressure changes. The data in each channel are expressed as percentage changes with respect to the mean value for that channel over the course of the experiment.

The individual data streams are offset from one another for clarity. The in vitro data for these experiments consists of average transmission readings over five minutes at each cell pathlength, as indicated by the micrometer setting.

For the in vivo data, three different Kolor metrics can be used for analysis, based on the observation that, to a first approximation, the transmission maxima represent the background transmission through the tissue and non-pulsatile blood, while the transmission minima represent the transmission through these two fractions, convolved with the absorbance due to the pulsatile blood fraction.

The first metric, representing the change in Kolor of the background absorption, is calculated as the percentage change in background transmission in each channel with respect to its initial value. In terms of the general definition of Kolor presented in the equation above, for this metric, $g(T_j)=(T_j-T_{j0})/T_{j0}$, where, for this metric, all transmission measurements in each detection channel are made at the peak value for each cardiac pulse.

The second metric that can be used represents the Kolor of the pulsatile fraction of the blood in a form analogous to that of pulse oximetry; i.e., the Kolor component in each detection channel is calculated as the change in transmission due to the pulse, relative to the background transmission. Mathematically, the function g for this metric is expressed as $g(T_j)=(T_{dj}-T_{sj})/T_{dj}$ where $T_{dj}$ and $T_{sj}$ represent the transmission levels in the jth detection channel at the diastolic and systolic blood pressure levels attained during each cardiac pulse.

The third metric that can be used calculates the Kolor of the pulsatile fraction of the blood as the change in transmission in each channel, without normalizing the change with respect to the background transmission. This is expressed mathematically as $g(T_j)=(T_{dj}-T_{sj})$.

In computing the Kolor using any of these metrics, a variety of averaging techniques can be used on the individual components of the measured Kolor to reduce the impact of data artifacts, caused by motion and other phenomena. The congruency and simultaneity of Kromoscopic measurements tend to cause such artifacts to occur in correlation in all the detection channels, thereby improving the performance of such averaging methods.

The first two metrics provided above also have an additional advantage. Since they both measure fractional changes in detection channel response, they are insensitive to changes in gain in the electronics or to changes in lamp output that do not result in changes in lamp color temperature.

To generate Kolors from the in vitro data for comparison with these Kolors, one can make use of the fact that, in the non-scattering medium of these in vitro experiments, the Beer-Lambert law applies:

$$I_{\lambda,1} = I_{\lambda,0} 10^{-\epsilon_\lambda C_B l}$$

where $I_{\lambda,1}$ is the intensity of the radiation transmitted by the sample, $I_{\lambda,0}$ is the intensity of the incident radiation, $C_B$ is the concentration of the absorbing analyte, l is the length of the sample, and $\epsilon_\lambda$ is the absorption coefficient.

Deviations from linearity due to the width of the detection band are estimated from measured water, detector, filter, and source spectra, and are typically negligible under the experimental conditions used. Therefore, changes in pathlength in vitro are equivalent to changes in concentration of the predominant absorbing species, water. Furthermore, at the high absorbance levels found for aqueous solutions in this spectral region, the logarithmic form of Beer's law is adequately approximated by a fractional change. The appropriate in vitro Kolors and Kolor changes are therefore calculated by measuring the change in transmission due to small changes in pathlength, either with or without normalization to the base transmission level, as needed.

These Kolor estimates are generated for each detection channel and for each individual pulse within each thirty-second data set. To reduce the impact of outliers due to motion artifacts, the median values for each data set are then used to represent the measured Kolor or Kolor change for that time period. The change in Kolor over the duration of the experiment, during which no conditions are altered, is computed by calculating the principal components of these medians. These principal components are then normalized to a unit vector, since here the Kolor changes are used for identification and comparison, and-not for quantitative analysis.

Results

Figure 5:
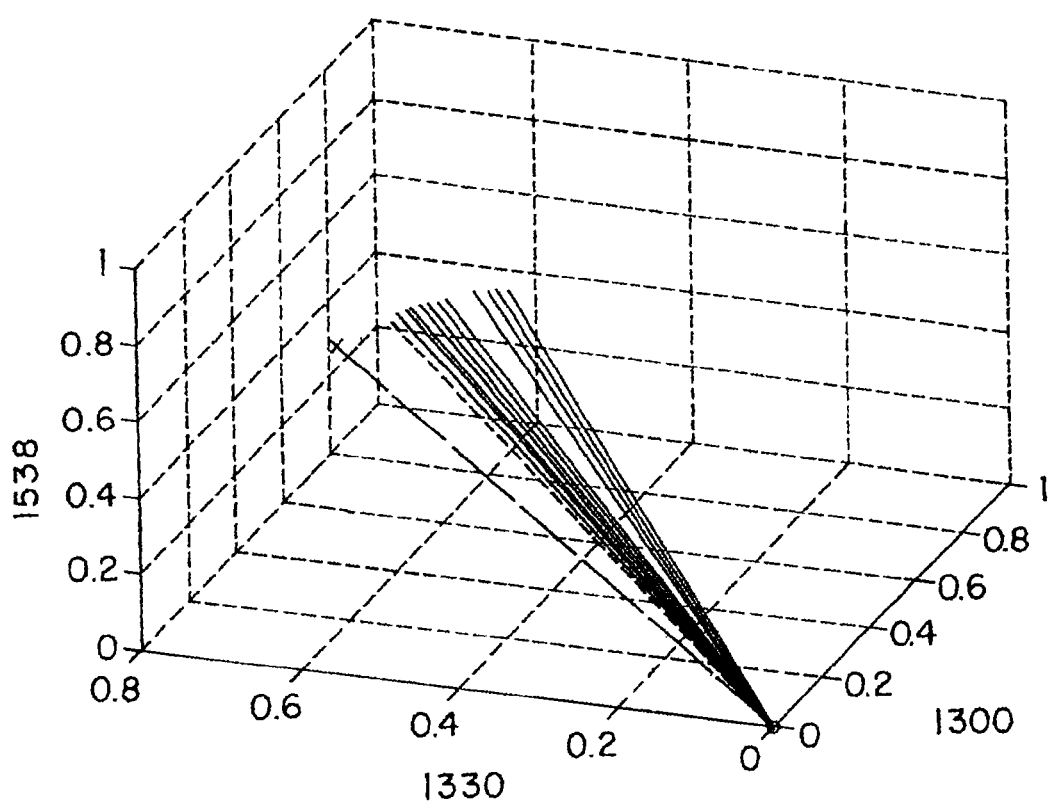
FIG. 5 shows results of Kolor measurements using a Kolor metric analogous to that of pulse oximetry.

FIG. 5 shows the results of the Kolor measurements using the Kolor metric analogous to that of pulse oximetry, wherein the fractional transmission change due to the cardiac pulse is normalized with respect to the background transmission. In all, seventeen experiments on fifteen different subjects were performed. It is seen that the in vivo Kolors (solid lines) (shown here for the Kolor space defined by the 1300, 1330, and 1538 filters) are fairly tightly grouped; a cone of less than 10 degrees includes all measured sample Kolor directions. The dashed line ending in a cross is the in vitro water Kolor direction, while the dotted line ending in a circle represents an estimate of the effects of scattering on the in vitro Kolor direction. This estimate will be discussed below.

Figure 6:
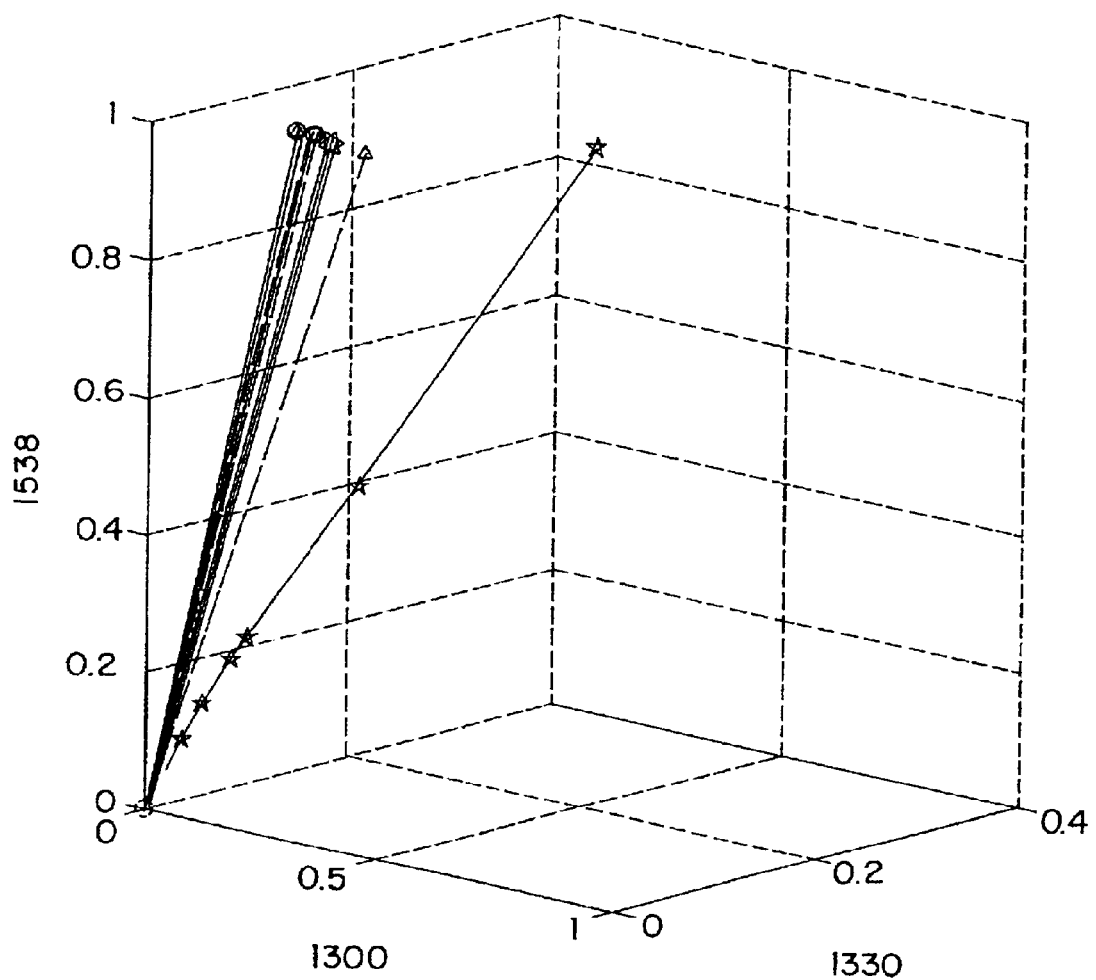
FIG. 6 shows results of Kolor measurements using a Kolor metric defined in terms of absolute changes in pulse transmission.

Referring to FIG. 6 another metric is employed relying on the absolute modulation Kolors (absolute difference between the transmission maxima and minima) for thirteen of seventeen data sets along with the in vitro measurements. Four data sets are not shown because a different source was used in those experiments. The absolute modulation metric is analogous to a color measurement where the color is dependent on the illuminant. Data taken with different sources with different color temperatures therefore cannot be directly compared using this metric. The same type and style of lamp and housing is used as the source for both the in vivo and in vitro experiments shown. For the absolute modulation metric, the measured Kolor is dependent on the pathlength as well, for the same reason. The in vitro water Kolors shown represent 1 mm pathlength changes at the various absolute pathlengths.

As with the metric shown in FIG. 5, the Kolor directions using the metric of FIG. 6 are tightly grouped, the average angular difference is less than 2 degrees and a cone of less than 6 degrees includes the sample Kolor directions of all thirteen subjects where the same source was used. At longer pathlengths (closer to the origin) the in vitro water Kolor for the 1 mm pathlength change is approximately 15° from the in vivo Kolors.

Figure 7:
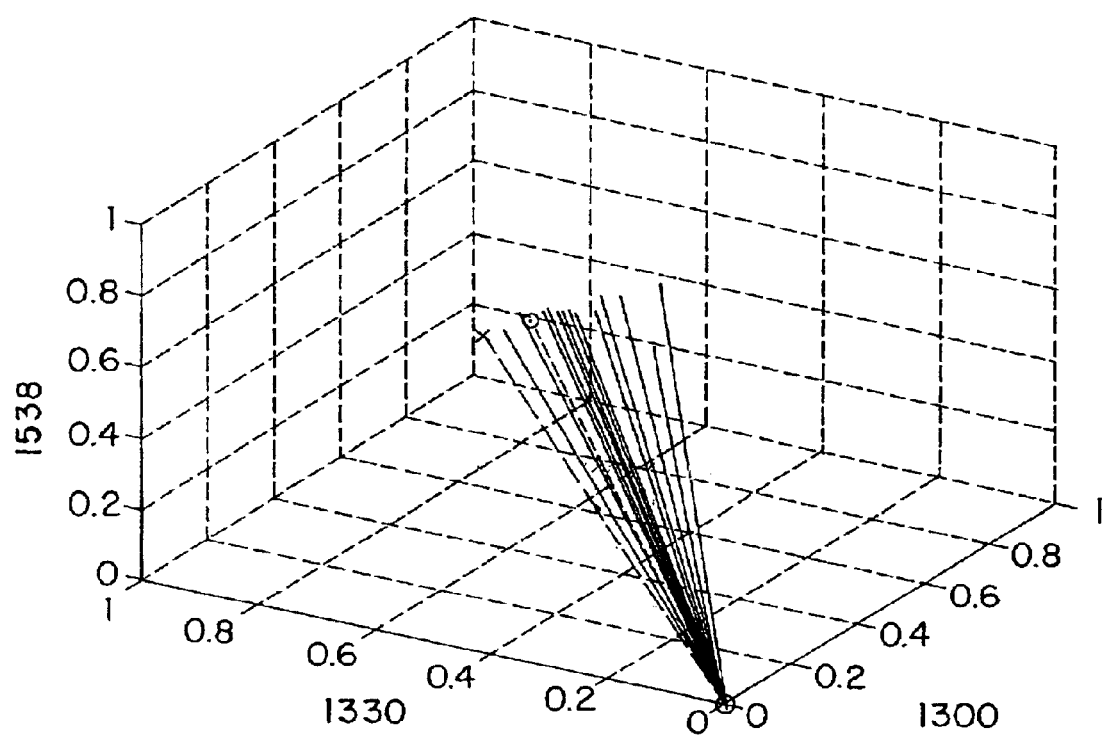
FIG. 7 shows results of Kolor measurements where the Kolor change of the background is estimated using the change in the background transmission in each detection channel, according to the teachings of the present invention.

FIG. 7 shows the same set of experiments as above. However, here the Kolor change of the background is estimated using the change in the background transmission in each detection channel. As seen in the normalized pulsatile transmission Kolor space shown in FIG. 5, the in vivo Kolors again fall into a cone, here somewhat larger than in the other Kolor spaces examined. The in vitro water Kolor, shown by the dashed line as in FIG. 5, is separated from the cone by a substantial angle. The dotted line, ending in a circle, again represents an estimate of the effects of scattering.

The angle $\theta$ between the in vitro Kolor direction for water and the in vivo color direction of the sample is small but significant in all three Kolor metrics. The angle $\theta$ is at least twice the angular spread of sample Kolor directions for seventeen runs on fifteen subjects.

One possible source for the angular disparity, $\theta$, between in vivo and in vitro Kolors is that the in vivo sample is not composed of pure water. Since the in vitro Kolor of water is being compared with the in vivo Kolor of the sample, the Kolor directions are expected to differ by the relative changes in concentration of all the absorbing species present in both the blood and the tissue background. However, further tests reveal that hemoglobin and oxyhemoglobin, the other major absorbers in the region, are not the predominant cause of the angular disparity, $\theta$.

Another possible source for the angular disparity, $\theta$, between in vivo and in vitro Kolors resides in the difference in optical pathlength between the two measurements. However, FIGS. 5 through 7 show that this is not the cause of the angular difference between in vitro and in vivo Kolors. The angular spread of the in vitro Kolor direction for a large range of path lengths, caused by differences in finger thicknesses, is only ⅓ of the angle $\theta$. Plots of the value of $\theta$ versus subject weight or subject gender, two likely correlates with finger size, also show no correlation with the angle $\theta$.

A third difference between the two measurement environments is the presence of scattering in the in vivo environment. It is well known that a change in the shape of the spectrum of a sample can be caused by the interaction of scattering and absorption. For example, in the weak absorption domain, stronger absorption features are more enhanced than are weak absorption features by the scattering. Photon diffusion theory, when applied to absorption combined with the highly forward scattering events occurring in vivo, indicates that scattering can be approximately incorporated into a one-dimensional tissue model by multiplying the physical pathlength by a multiplier proportional to the square root of the ratio of the scattering to the absorption coefficient at the wavelength of interest. If it is further assumed that the scattering coefficient is not a function of wavelength over the range of wavelengths covered by the Kromoscopic detection channels, then, to a rough approximation, the components of the Kolor of water in a highly scattering medium are proportional to the square roots of the Kolor components in a non-scattering medium.

Application of this model to the in vitro data results in the dotted lines shown in FIGS. 5 and 7 above. In both cases, the correction indicated by the model predicts a rotation of the Kolor in general agreement with the change measured from in vitro to in vivo conditions, suggesting that the presence of scattering is the predominant cause of the angle θ being greater than zero.

In contrast to the significant angle between the average in vivo Kolor vector and the in vitro Kolor vector, the angle spread among the in vivo Kolor vectors is small, and indicative of measurement stability. The small angular spread can be seen across fifteen different subjects measured with two different instruments over a period of four months. Additional data, not presented here, shows similar small angular spreads for other Kolor spaces measured across different fingers of the same subject as well as between subjects.

Given the uniqueness of the Kolors in a given Kolor space and metric, Kolor stability is what is required in order to clearly identify a given analyte. However, in the analytical problem under discussion here, the presence of the non-zero angle θ spoils the opportunity to directly use Kolor identification in vitro as a method of identifying species in vivo. If the value of θ were zero, a subject-independent calibration would be possible, at least for purposes of analyte identification. Using principles of the present invention, which are now explained, it is nonetheless possible to obtain the concentration of an analyte in a scattering medium.

Calculation of Analyte Concentration in a Scattering Medium

As can be seen from FIG. 5, the Kolor vector of an analyte in a scattering medium such as blood (any of the solid lines) is not coincident with the Kolor vector of the analyte in a non-scattering medium (the line ending with a cross). The average Kolor vector pertaining to the scattering medium can be made co-directional with the Kolor vector pertaining to the non-scattering medium by a rotation that can be specified by a correction vector $\Delta$. (Note that the specification of the rotation can not be made only by the angle θ, which defines a cone, but instead requires three variables, such as the three Euler angles, given by $\Delta$; in a Kolor space of larger dimension than three, more variables are required to specify the rotation). A useful property of $\Delta$ is that it is independent of the particular analyte being measured. Thus, having obtained $\Delta$ using water as a standard, the Kolor vector of a trace analyte, such as glucose, obtained in a subsequent measurement performed with a scattering medium can be transformed to its corresponding in vitro Kolor vector by a rotation $\Delta$. A standard, such as water, can therefore be used to obtain a correction vector that transforms data obtained in the scattering medium to corresponding data in a non-scattering medium.

Thus, if the discrepancy between the scattering and non-scattering Kolor vectors is the result of changes in water pathlength, then the rotation specified by $\Delta$ applies equally to all the minor chemical constituents in the sample as well, since the rotation is produced by the interaction of the scattering and the overall absorption coefficient, not the absorptions of each species. The Kolor of any species of interest in vivo can be derived from its in vitro Kolor and the rotation $\Delta$ of the water Kolor. This process can be carried out in a Kolor space of any number of dimensions. With the Kolor uniquely identified in vivo, specific analyte identification is possible.

For example, using water as a standard and performing Kolor vector measurements such as those of FIG. 5 allow a determination of $\Delta$. A subsequent in vivo measurement of the glucose Kolor vector yields a vector $v_s$, where the subscript denotes "scattering." The vector $v_s$ is subjected to a rotation specified by $\Delta$, yielding the vector $v_{ns}$, where the subscript denotes "non-scattering." The vector $v_{ns}$ can be associated with a particular concentration of the glucose, as detailed in U.S. Pat. No. 5,424,545, in analogy to how each vector in the CIE calorimetric space is associated with a color.

Figure 8:
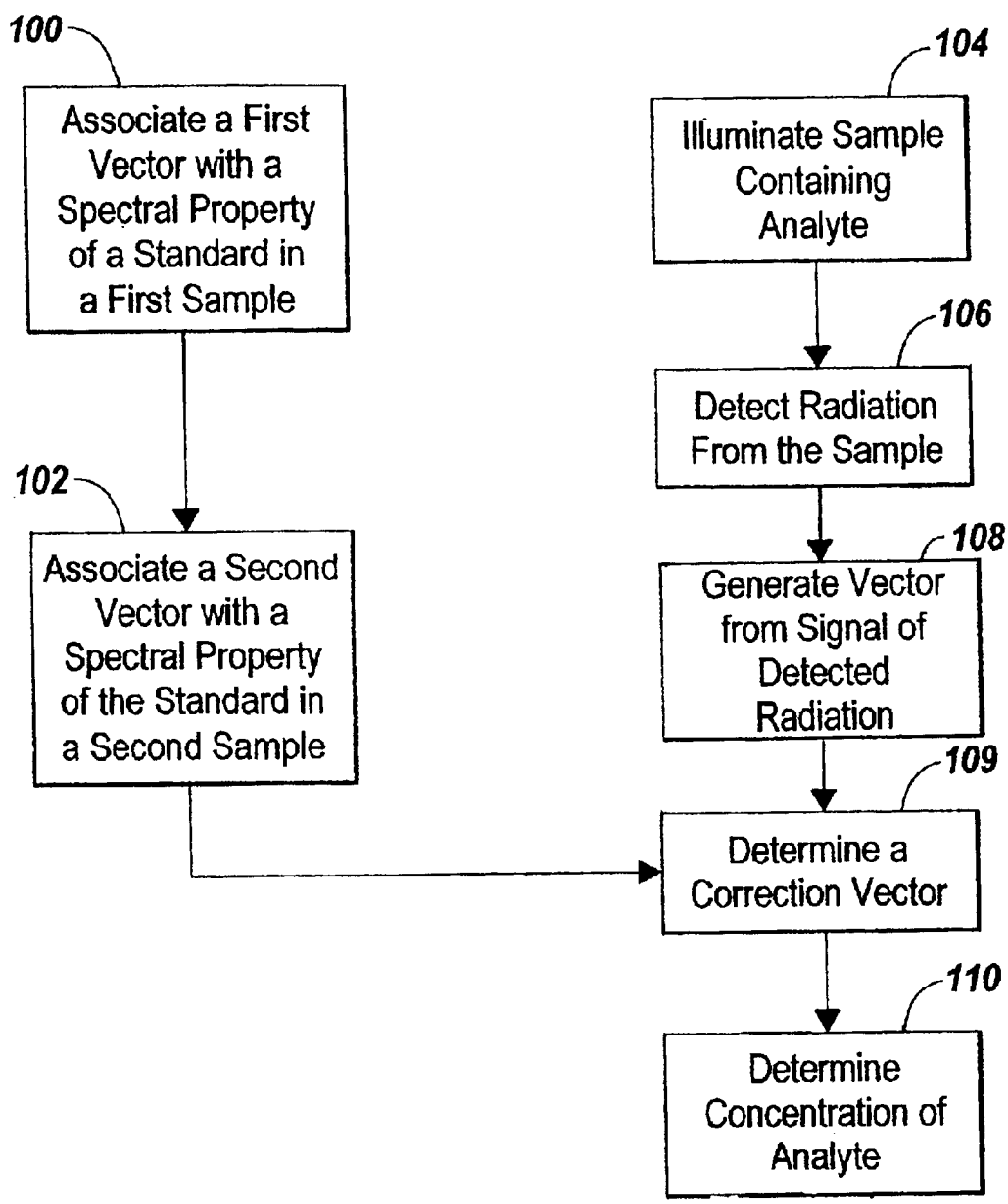
FIG. 8 shows a flow chart for measuring the concentration of an analyte in a scattering medium, according to the teachings of the present invention.

The independence of the rotation, specified by $\Delta$, on the analyte, whether or not such a rotation arises from scattering effects, allows a method for measuring the concentration of an analyte. After $\Delta$ is found using a standard, the rotation can be applied to each of the minor chemical constituents in the sample. The method is presented as a flow chart in FIG. 8. In step 100, the first measurement stage 12 determines a first vector associated with a first spectral property of a standard in a first sample. This first vector can be the Kolor in Kolor space of a standard, such as water. Moreover, this first vector can be obtained in vitro in the presence of a non-scattering medium. Such a first vector is shown in FIG. 5 as the dashed line ending with a cross.

In step 102, the second measurement stage 14 determines a second vector. The second vector is associated with a second spectral property of the standard in a second sample containing the scattering medium. The second vector can be obtained in vivo, where blood is the scattering medium of interest. Such a second vector can be taken to be the average of the solid line vectors shown in FIG. 5. Alternatively, vectors can similarly be obtained using the other metric of FIG. 7.

As mentioned above, the second vector is displaced from the first vector by a rotation specified by $\Delta$, which is determined by the analyzer 22 in step 109 below. The correction vector $\Delta$ can be used to find the concentration of an analyte of interest in a scattering medium in vivo.

In particular, in step 104 a sample containing the scattering medium, in which is present the analyte, such as glucose, is illuminated with broad spectrum radiation. Next, in step 106, transmitted, transflected, or reflected radiation is detected from the sample. In step 108, a signal is generated by the generator 20 corresponding to the detected radiation, which signal can be used by the generator 20 to form a vector in Kolor space. In step 109, the analyzer 22 determines a correction vector $\Delta$ from the standard in a substantially non-scattering medium from the previous measurements of the first and second vectors. Subsequently, in step 110, the analyzer 22 determines the concentration of the analyte in the scattering medium by utilizing the correction vector and the vector associated with the amount of transmitted, transflected, or reflected radiation.

For example, the first and second vectors allow the computation of $\Delta$, the rotation that transforms the second vector so that it is coincident with the first vector. The signal, corresponding to a subsequent in vivo measurement can be used to find the Kolor of the analyte of interest, which is the vector associated with the amount of transmitted, transflected, or reflected radiation. In particular, the vector of the analyte of interest is transformed by the rotation specified by $\Delta$, yielding the corresponding Kolor vector of the analyte in a non-scattering medium. From this Kolor vector of the analyte, the analyzer 22 can deduce the corresponding concentration.

Some of the apparatus utilized to obtain the signal associated with the in vivo measurement of the analyte can be the same as the apparatus in the first and second measurement stages 12 and 14 described above. For example, the light source 16 shown in FIG. 1 can coincide with the light source 48 shown in FIG. 2 that is present in the first measurement stage 12 to shine infrared light on the first sample. Similarly, the detector 18 shown in FIG. 1 can coincide with the four-channel assembly 40 shown in FIG. 2 having the photodiodes 42.

The foregoing description invention is meant to be explanatory only and not intended to be limited to the scope of the invention. The invention is defined by the following claims.

What is claimed is:

1. A method for measuring the concentration of an analyte in a scattering medium, the method comprising the steps of:
   illuminating a sample containing said analyte with broad spectrum radiation;
   detecting an amount of transmitted, transflected, or reflected radiation from the sample with a detector;
   associating a vector in a vector space with the amount of transmitted, transflected, or reflected radiation;
   determining a correction vector from a measurement of a standard in a non-scattering medium as compared with the measurement of the same standard in the scattering medium; and
   utilizing said correction vector and said vector associated with the amount of transmitted, transflected, or reflected radiation to identify and to obtain the concentration of the analyte in the scattering medium.

2. The method of claim 1, wherein said detecting step includes impinging the radiation transmitted, transflected, or reflected from the sample onto the detector that includes a plurality of detection units each responsive to a specific region of a spectrum associated with the transmitted, transflected, or reflected radiation, the spectral response of each of said detection units having at least partial overlap with the response of at least one other of said detection units.

3. The method of claim 2, wherein at least three detection units are used in said detecting step, each detection unit having a peak spectral response in a separate portion of said spectrum.

4. The method of claim I wherein said detecting step includes impinging the radiation transmitted, transflected, or reflected from the sample onto the detector that includes a plurality of filters, each of said filters allowing transmission of a specific region of a spectrum associated with the transmitted, transflected, or reflected radiation, the spectral response of each of said filters having at least partial overlap with the response of at least one other of said filters, wherein each of said filters is impinged on the radiation transmitted, transflected, or reflected from said sample or standard sequentially and the output from said detector is used to measure the concentration.

5. The method of claim 1, wherein said detector comprises broad bandpass filters.

6. The method of claim 1, wherein said detecting step further comprises the use of a black/white detection unit which is responsive to the entire spectrum for which said detector has a spectral response.

7. The method of claim 1, wherein the step of utilizing includes utilizing an artificial analog of a neural network.

8. The method of claim 7, wherein said artificial neural network is calibrated and trained to process said signals to achieve an analog of color constancy in vision.

9. The method of claim 1, and wherein said method is used to non-invasively determine the concentration of the analyte in a human body.

10. The method of claim 1, wherein said analyte is selected from the group consisting of glucose, glucose indicating constituents, hemoglobin, and hemoglobin indicating constituents.

11. The method of claim 1, wherein said analyte is selected from the group consisting of drugs of abuse and drugs of abuse indicating constituents.

12. The method of claim 1, wherein the sample includes a portion of a finger.

13. The method of claim 1, wherein the correction vector is obtained by obtaining a first vector associated with a first spectral property of the standard in the non-scattering medium; and
   obtaining a second vector associated with a second spectral property of the standard in a second sample containing the scattering medium.

14. The method of claim 13, wherein the first vector and the second vector both belong to a vector space whose dimension is equal to the number of detection units in the detection array.

15. The method of claim 14, wherein the step of utilizing includes calculating a rotation that transforms the second vector into the first vector, said rotation specifying the correction vector.

16. The method of claim 13, wherein the second sample is in vivo.

17. The method of claim 1, wherein the standard in the non-scattering medium is in vitro.

18. The method of claim 1, wherein the sample is in vivo.

19. The method of claim I, wherein the vector space has a dimension that is equal to the number of detection units.

20. A system for measuring the concentration of an analyte in a scattering medium, the system comprising:
   a light source for illuminating a sample containing said analyte with broad spectrum radiation;
   a detector for detecting an amount of transmitted, transflected, or reflected radiation from the sample;
   a generator for generating a vector in a vector space that is associated with the amount of transmitted, transflected, or reflected radiation; and
   an analyzer for determining a correction vector from a measurement of a standard in a non-scattering medium as compared with the measurement of the same standard in the scattering medium, and for utilizing said correction vector and said vector associated with the amount of transmitted, transflected, or reflected radiation to identify and to obtain the concentration of the analyte in the scattering medium.

21. The system of claim 20, wherein the detector includes a plurality of detection units each responsive to a specific region of a spectrum associated with the transmitted, transflected, or reflected radiation, the spectral response of each of said detection units having at least partial overlap with the response of at least one other of said detection units.

22. The system of claim 21, wherein the detector includes at least three detection units, each detection unit having a peak spectral response in a separate portion of said spectrum.

23. The system of claim 20, wherein the detector includes a plurality of filters, each of said filters allowing transmission of a specific region of a spectrum associated with the transmitted, transflected, or reflected radiation, the spectral response of each of said filters having at least partial overlap with the response of at least one other of said filters, wherein each of said filters is impinged on the radiation transmitted, transflected, or reflected from said sample or standard sequentially and the output from said detector is used to measure the concentration.

24. The system of claim 20, wherein said detector comprises broad bandpass filters.

25. The system of claim 20, wherein the detector includes a black/white detection unit which is responsive to the entire spectrum for which said detector has a spectral response.

26. The system of claim 20, wherein the analyzer includes an artificial analog of a neural network.

27. The system of claim 26, wherein said artificial analog of a neural network is calibrated and trained to process said signals to achieve an analog of color constancy in vision.

28. The system of claim 20, wherein said system is used to non-invasively determine the concentration of the analyte in a human body.

29. The system of claim 20, wherein said analyte is selected from the group consisting of glucose, glucose indicating constituents, hemoglobin, and hemoglobin indicating constituents.

30. The system of claim 20, wherein said analyte is selected from the group consisting of drugs of abuse and drugs of abuse indicating constituents.

31. The system of claim 20, wherein the sample includes a portion of a finger.

32. The system of claim 20, wherein the analyzer obtains the correction vector by utilizing a first vector associated with a first spectral property of the standard in the non-scattering medium; and a second vector associated with a second spectral property of the standard in a second sample containing the scattering medium.

33. The system of claim 32, wherein the first vector and the second vector both belong to a vector space whose dimension is equal to the number of detection units in the detection array.

34. The system of claim 33, wherein the analyzer calculates a rotation that transforms the second vector into the first vector, said rotation specifying the correction vector.

35. The system of claim 32, wherein the second sample is in vivo.

36. The system of claim 20, wherein the standard in the non-scattering medium is in vitro.

37. The system of claim 20, wherein the sample is in vivo.

38. The system of claim 20, wherein the vector space has a dimension that is equal to the number of detection units.

* * * * *